United States Patent

Bitowft et al.

[11] Patent Number: 5,772,813
[45] Date of Patent: Jun. 30, 1998

[54] METHOD FOR MAKING AN ABSTRACT ARTICLE COMPRISING AN ABSORBENT CORE HAVING TWO TYPES OF FIBERS AND FIBERBOARD FOR USE IN SUCH A METHOD

[75] Inventors: Bruce Kevin Bitowft, Glashuetten; Karsten Puchert, Griesheim, both of Germany

[73] Assignee: The Procter & Gamble Company, Cincinnati, Ohio

[21] Appl. No.: 678,142

[22] Filed: Jul. 11, 1996

Related U.S. Application Data

[63] Continuation of Ser. No. 331,546, Sep. 12, 1995, filed as PCT/US93/03889, Apr. 26, 1993, published as WO93/21968, Nov. 11, 1993, abandoned.

[30] Foreign Application Priority Data

May 6, 1992 [EP] European Pat. Off. ............... 92870068

[51] Int. Cl.$^6$ ........................................ A61F 13/00
[52] U.S. Cl. .................... 156/62.4; 156/62.2; 264/116; 264/122; 428/362; 428/369
[58] Field of Search ................. 156/62.4, 62.2; 264/116, 122; 428/362, 369; 604/370

[56] References Cited

U.S. PATENT DOCUMENTS

| | | | |
|---|---|---|---|
| 4,241,881 | 12/1980 | Laumer | 241/28 |
| 4,674,966 | 6/1987 | Johnson et al. | 425/82.1 |
| 4,902,463 | 2/1990 | Tanaka et al. | 264/122 |
| 4,957,795 | 9/1990 | Riedel | 428/74 |
| 5,064,484 | 11/1991 | Craig et al. | 156/62.6 |
| 5,102,501 | 4/1992 | Eber et al. | |
| 5,316,601 | 5/1994 | Hebbard et al. | 264/116 X |

*Primary Examiner*—Michael W. Ball
*Assistant Examiner*—Sam Chuan Yao
*Attorney, Agent, or Firm*—Theodore P. Cummings; Kevin C. Johnson; Steven W. Miller

[57] ABSTRACT

In a process of making an absorbent article such as a sanitary napkin or a disposable diaper, hydrophilic fibers and crimped or coiled synthetic fibers are supplied in a single fiberboard to a defiberising means such as a hammermill. The process results in a homogenous and resilient blended absorbent core that can be produced using a single defiberising unit. The crimped or coiled fibers pass through the defiberising means without their two or three-dimensional structure being adversely affected at a relatively low defiberisation energy.

7 Claims, 2 Drawing Sheets

METHOD FOR MAKING AN ABSTRACT ARTICLE COMPRISING AN ABSORBENT CORE HAVING TWO TYPES OF FIBERS AND FIBERBOARD FOR USE IN SUCH A METHOD

This is a continuation of application Ser. No. 08/331,546, filed as PCT/US93/03889, Apr. 26, 1993, published as WO93/21968, Nov. 11, 1993, now abandoned.

FIELD OF THE INVENTION

The invention relates to a method for making absorbent articles comprising a liquid-pervious topsheet, a liquid-impervious backsheet, and an absorbent core interposed between the topsheet and the backsheet, the absorbent core comprising a first type of fibers that are hydrophilic and a second type of fibers that are synthetic, the two types of fibers having been mixed and compressed to form a fiber board, the method comprising the step of supplying the fiber board to a defiberising means for forming individualised fibers or groups of fibers.

The invention also relates to a fiber board for use in such a method.

BACKGROUND OF THE INVENTION

A method for making an absorbent article by defiberisation of a fiber board comprising a mix of cellulosic fibers and polyethylene terephthalate (PET) fibers, is described in a brochure edited by Du Pont International SA, 2 chemin du Pavillon, P.O. Box 50, CH-1218 Le Grand-Saconnex, Geneva. The fiber boards are marketed by the Metsa-Serla Group, Lielahti Pulp Mill, P.O. Box 436, SF-332101 Tampere under the registered trade mark SPHINX "FLUFF D".

In the above-given brochure it is described that such absorbent cores have a relatively high dry and wet net-work strength compared to sulphite and sulphate pulps. Absorbent cores comprising PET-fibers have a good absorption capacity and relatively high resiliency under load, which provides for better moisture retention and softness due to its open structure. The defiberisation energy of fiber boards comprising cellulosic fibers and PET-fibers is relatively low compared to the defiberisation energy of sulfate pulp fiber boards.

It is an object of the invention to provide a method of producing an absorbent article having a relatively resilient absorbent core.

It is another object of the invention to provide a method of producing an absorbent article comprising a core having at least two types of fibers that in the absorbent core form a homogeneous mixture.

It is another object of the invention to provide an efficient method of producing the above mentioned absorbent articles.

SUMMARY OF THE INVENTION

In the method according to the invention, the fiber board comprises at least 10% by weight of synthetic fibers that are of generally two dimensional or three dimensional structure and have an average extended length of between 2 and 25 mm, a denier of between 6 and 40, preferably between 10 and 20 and between 3 and 8 crimps or coils per inch.

The generally two dimensional, crimped, structure or generally three dimensional, coiled, structure of the synthetic fibers gives to a core an increased resiliency compared to cores using synthetic fibers of generally one dimensional structure. Surprisingly, the physical properties of the synthetic fibers is maintained when the fibers are compressed into a fiber board of for instance a density of 0.45 gcm$^{-3}$ and a caliper of 1.7 mm, and are later defiberised in defiberising means such as hammer mills, disc mills or rotor mills. Without wanting to be bound by any theory, it is believed that because of the relatively long fiber length, the synthetic fibers have sufficient flexibility to be able to absorb a certain amount of defiberisation energy by flexing or banding before the crimped or the coiled structure of the fibers is destroyed by plastic deformation, caused by the defiberising means.

Because of the relatively large denier of the synthetic fibers, their resistance against deformation by the defiberisation means is high. Surprisingly, the defiberisation energy of the fiber boards comprising the relatively long and irregularly shaped fibers, was found to be about 10% lower than the defiberisation energy of the known fiber boards comprising straight synthetic fibers. The relatively low defiberisation energy that needs to be supplied for individualising the fibers of the fiber boards, is believed to result in the synthetic fibers passing relatively undamaged through the defiberisation means.

The supply of a number of different fibers in a single fiber board, reduces the number of necessary defiberising means. In U.S. Pat. No. 5,004,579, assigned to McNeil PPC-Inc, two types of fiber boards, each consisting of single type of fibers, are supplied to two separate defiberising means. After defiberisation, the fibers are air-entrained via separate ducts and air-laid on a foraminous surface of a rotating vacuum drum. By combining, according to the invention, both type of fibers in a single fiber board, only a single defiberising means is necessary. In this case, a homogenous mixture of fibers is obtained, without the need of additional measures to ensure homogenous mixing of the fibers before lay-down, as would be necessary in the case when fibers are supplied from separate defiberising means.

The concentration of synthetic fibers in the fiber board lies between 10 and 40% by weight, preferably around 20%. For this concentration, the absorbent core has the desired resiliency, whereas the defiberisation energy of the fiber board is sufficiently low to prevent damage of the synthetic fibers upon defiberisation.

In an embodiment of the method according the invention, the fibers are after defiberisation passed through a filter means, such as a mesh or a perforated plate, to prevent lumps of undefiberised fibers from getting into the absorbent core. Despite the relatively long and irregularly shaped synthetic fibers used, it was surprisingly found that conventional filter means, such as described in U.S. Pat. No. 3,966,126, issued to Werner, could be used without being blocked by the fibers.

BRIEF DESCRIPTION OF THE DRAWINGS

The invention will be described in detail with reference to the accompanying drawings. In the drawings.

DETAILED DESCRIPTION OF THE INVENTION

Figure 1:
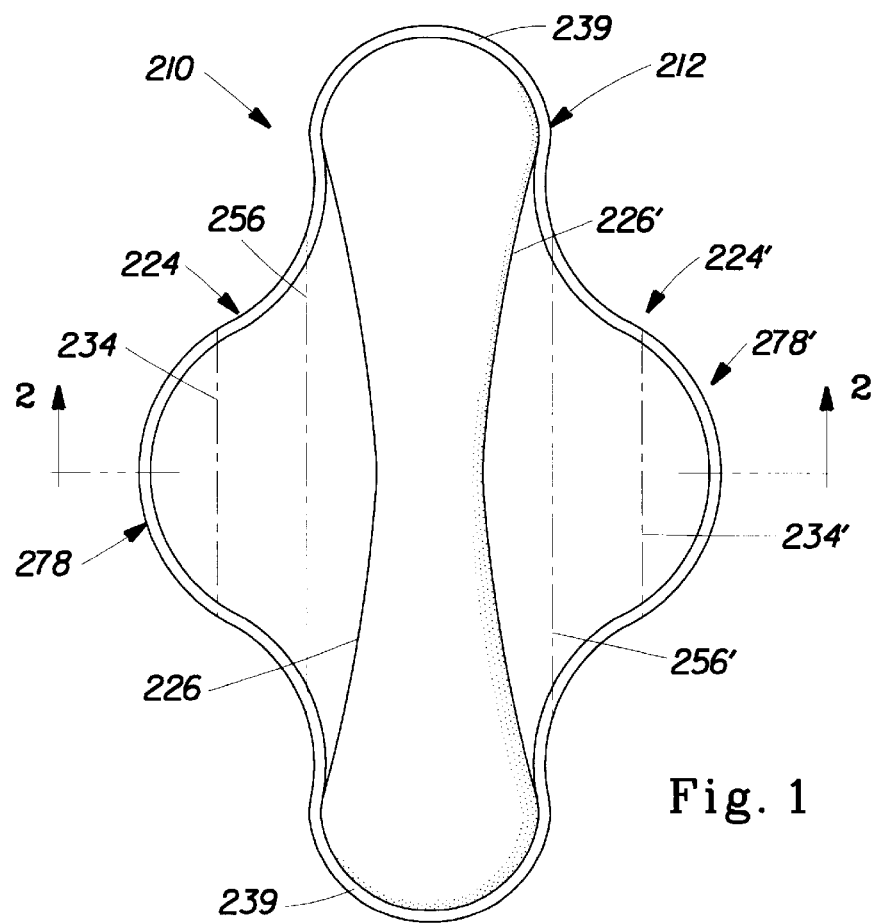
FIG. 1 shows a plan view of an absorbent article.

Although the absorbent article referred to in the drawings is a sanitary napkin, the invention is not limited thereto but extends to absorbent products in general such as for instance disposable baby diapers or incontinence briefs that are made by the method according to the invention. The absorbent products can comprise absorbent cores of any general shape and configuration.

Figure 2:
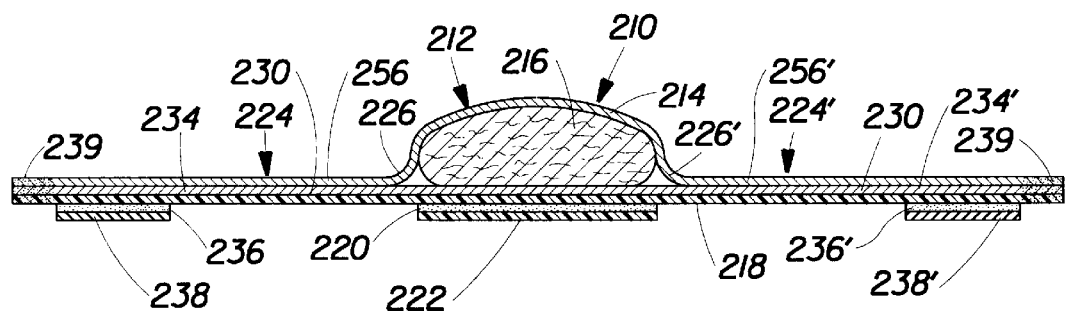
FIG. 2 shows a cross sectional view of the absorbent article of FIG. 1 along the line 2 and FIG. 3 shows an apparatus for use in a method of manufacturing an absorbent article according to the invention.

FIGS. 1 and 2 show a sanitary napkin 210 comprising an absorbent means represented by central absorbent pad 212 and two flaps 224 and 224'. Flap 224 is associated with central absorbent pad 212 along nonlinear line of juncture 226. As used in the context of the present specification, the term "nonlinear" refers to any of various curve, as opposed to straight lines. Flap 224 has distal edge 278 which is remote from line of juncture 226. In the embodiment illustrated in FIG. 1, line of juncture 226 is concave relative to distal edge 278. That is to say, line of juncture 226 curves away from distal edge 278. In this embodiment, nonlinear lines of juncture 226 and 226' and seam 239 define an absorbent means (central absorbent pad 212) which is narrower in its central region than at its ends. A sanitary napkin narrower in the center that at the ends is generally perceived by the user as more comfortable than sanitary napkin of uniform width.

As shown in FIG. 2, central absorbent pad 212 comprises absorbent core 216. Central absorbent pad 212 and flap 224 both comprise topsheet 214. In effect, topsheet 214 forms one surface of flap 224 while backsheet 218 forms the other surface; topsheet 214 also forms one surface of central absorbent pad 212, backsheet 218 the other. In the embodiment illustrated, flap absorbent core 230 is interposed between topsheet 214 and backsheet 218. Topsheet 214 and backsheet 218 are joined at seam 239 around the entire periphery of sanitary napkin 210. The purpose of this seam is to unite the various elements of the sanitary napkin into a whole. Topsheet 214 is secured to flap absorbent core 230 and backsheet 218 along nonlinear lines of juncture 226 and 226' by attachment means not illustrated in FIG. 2. Illustrated in FIG. 2 are the adhesive attachment means central pad adhesive 220 and flap adhesive 236 which are covered by, respectively, central pad release liner 222 and flap release liner 238. These adhesive attachment means are adapted to secure sanitary napkin 210 within the crotch region of an undergarment. Topsheet 214 is liquid permeable and, when sanitary napkin 210 is in use, is in close proximity to the skin of the user. topsheet 214 is compliant, soft feeling and non-irritation to the user's skin. It can be made from any of the materials conventional for this type of use. Non-limiting examples of suitable materials that can be used as topsheet 214 are woven and non-woven polyester, polypropylene, nylon, and rayoon and formed thermoplastic films; formed films are preferred. suitable formed films are described in U.S. Pat. No. 4,324,246 and U.S. Pat. No. 4,342,314, both patents which are incorporated herein by reference. Formed films are preferred for topsheet 214 because they are pervious to liquids and yet non-absorbent. thus, the surface of the formed film, which is in contact with the body, remains dry and is more comfortable to the wearer.

The surface of the topsheet 213 can be treated with a surfactant. Treating the outer surface of the topsheet with surfactant renders the surface more hydrophilic which results in liquid penetrating the topsheet faster than if the surface were not treated. This diminishes the likelihood that menstrual fluid will flow off topsheet 214 rather than being absorbed by the absorbent core 216. It is preferred that the surfactant be substantially evenly and completely distributed across the outer surface of the topsheet 214. This can be accomplished by any of the common techniques well known to those skilled in the art. For example, the surfactant can be applied to topsheet 214 by spraying, by padding, or by the use of transfer rolls.

Preferably, the inner surface of the topsheet 214 is secured in contacting relation to absorbent core 216. This contacting relationship results in liquid penetrating topsheet 214 faster than if it were not in contact with the absorbent core 216. Topsheet 214 can be maintained in contact with absorbent core 216 by applying adhesive, preferably in spaced, limited areas, to the inner surface of the topsheet 214. Examples of suitable adhesives used for this purpose include the acrylic emulsion E-1833 BT manufactured by Rohm and Haas Company of Philadelphia, Pa. and the acrylic emulsion WB3805 manufactured by H.B. Fuller Company of St. Paul, Minn.

Referring to FIG. 2, it can be seen that absorbent core 216 is positioned between topsheet 214 and backsheet 218. Backsheet 218 is impervious to liquids and prevents body fluids which may be expressed from the absorbent core 216 from soiling the clothing of the user. Any material used in the art for such purpose can be utilized herein. Suitable materials are embossed or nonembossed polyethylene films and laminated tissue. The outer surface of backsheet 218, generally in register with absorbent core 216, is coated with central pad adhesive 220. Central pad adhesive 220 provides an adhesive attachment means for securing central absorbent pad 212 in the crotch portion of a panty. Any adhesive or glue used in the art for such purpose can be used herein, with pressure sensitive adhesives being preferred. Suitable adhesives are Century A-305-IV manufactured by the Century Adhesives Corporation and Instant Lok 34-2823 manufactured by National Starch Company. The pressure sensitive adhesive of central pas adhesive 220 should be covered with central pad release liner 222 to keep the adhesive from drying out and to keep it from sticking to extraneous surfaces prior to use. Any commercially available release liner commonly used for such purposes can be used herein. Nonlimiting examples of suitable release liners are BL 30 MG-A Silox E1/0 and BL 30 MG-A Silox 4 P/O both of which are manufactured by the Akrosil Corporation. The outer surface of flap 224, adjacent distal edge 278, is coated with flap adhesive 236 that is covered by a removable flap release liner 238.

The absorbent core 216 can comprise next to the synthetic, crimped or coiled fibers any material used in the art. Examples include natural materials such as cotton, comminuted wood pulp which is generally referred to as airfelt, creped cellulose wadding, peat moss, cross-linked cellulose fibers, synthetic staple fibers, polymeric fibers, hydrogel-forming polymer gelling agents, or any equivalent material or combinations of materials. The polymeric gelling agent which is employed in the absorbent core 216, will generally comprise particles of a hydrogel-forming polymer material. The term 'particles', as used herein can refer to particles in any form, such as in the form of pellets, flakes, or fibers. Further characteristics of the absorbent core 216 are described in detail in U.S. Pat. No. 4,673,402, issued to Weisman et al and U.S. Pat. No. 5,009,653 issued to Osborn which patents are incorporated herein by reference.

The absorbent core 216 according to the invention is a so-called blended core. This particular core arrangement is shown in a relatively thick sanitary napkin 210, but it can, however also be formed in a thin web for use in thin products.

According to the invention, the core 216 comprises a batt of fibers, preferably in the form of a homogeneous blend of fibers. The blended core 216 is comprised of at least two groups (or types) of fibers. These include a first group of low denier, relatively short, hydrophilic fibers, and from about 10%, to about 90% of higher denier, longer synthetic fibers that comprise a second group (or type) of fibers. The blend ratio of the two groups of fibers can be varied to produce the properties desired for different types of absorbent articles. (All percentages specified in this description are by weight unless stated otherwise).

The first group of fibers can comprise natural fibers such as cotton, cellulose or other natural fibers. The first group of fibers can alternatively or additionally comprise synthetic fibers, including but not limited to, rayon, chemical thermal mechanical pulp (or "CTMP" or "MP"), ground wood, or chemically modified fibers, such as cross-linked cellulose fibers. Suitable cross-linked cellulose fibers are described in U.S. Pat. Nos. 4,822,543, 4,888,093, 4,889,595, 4,898,642 and 4,935,022.

The fist group of fibers preferably comprises comminuted wood pulp fibers known as airfelt. The fibers in the first group of fibers are either inherently hydrophilic, or they may be rendered hydrophilic for instance by treating them with a surfactant. Performance is improved by selecting a relatively stiff fiber which maintains a substantial portion of its compression resistance when wetted (that is, the fibers should have a high compressive modulus). Preferably, the fibers selected are both compression resistant and wet and dry resilient (i.e., they tend to both resist compression and to spring back when compressed). Cross-linked cellulose fibers are especially preferred for these criteria. (It is understood, however, that cross-linked cellulose fibers are sufficiently modified that they may no longer be considered as either cellulosic, or as natural fibers, per se).

The second group of fibers should all be of high compressive modulus and should maintain a relatively high modulus when wetted. The second group of fibers should also preferably be wet and dry resilient.

Suitable synthetic fibers include polyester, polypropylene, polyethylene, nylon, viscous rayon fibers or cellulose acetate, with polyester being preferred. The fibers in the second group are longer than the fibers in the first group of fibers. Preferably, the fibers in the second group of fibers have a length of at least about 0.6 cm (¼ inch) and more preferably at least about 1.3 cm (½ inch). The denier of the fibers in the second group of fibers is preferably bigger than the denier of the fibers in the first group of fibers. The fibers in the second group of fibers have a denier of between 6 and 40, preferably between 15 and 30, most preferably between 15 and 25.

The fibers in the second group may be hydrophilic, hydrophobic, or partially hydrophilic and partially hydrophobic. The fibers in the second group of fibers preferably have at least some hydrophilic component (preferably a cellulosic component). The fibers in the second group of fibers can be provided with a hydrophilic component in a number of suitable ways. These include, but are not limited to coating or treating the fibers to render them, or at least their surfaces, hydrophilic.

One suitable type of synthetic fibers for use in the second group of fibers are crimped polyester fibers. Suitable synthetic fibers are available from Eastman Kodak Textile Fibers Division Kingsport, Tenn. as the KODEL 200 and 400 series. One suitable type of synthetic fiber is the KODEL 410 fiber. A suitable polyester fiber is the KODEL 431 fiber. These KODEL fibers are preferably crimped at a crimping frequency of between about 5 and 78, preferably about 6, more preferably 6.3 crimps per linear inch. The fibers are preferably crimped at a crimping angle of between about 70° and 91°, preferably about 88°. Crimping provides the fibers with improved resilience, among other desired properties. The fibers have a denier of 15 per filament and a length of about 1.3 cm (½ inch). They may be coated with a hydrophilic or hydrophobic finish by any suitable method known in the art.

In an alternative embodiment, it is possible to replace the cellulose fibers in the first group of fibers with very short, low denier synthetic fibers (with hydrophilic surfaces). The blended core 216 in this situation would consist of short, low denier, hydrophilic first group of synthetic fibers (such as polyester fibers with a CELWET finish) and long, high denier second group of synthetic fibers. Such a blended core may also contain particles of hydrogel-forming polymer gelling agents to increase the absorptive capacity of the core.

In one preferred embodiment, the hydrogel-forming polymer gelling agents comprise "high speed" absorbent gelling materials. The term "high-speed" absorbent gelling materials, as used herein, means those absorbent gelling materials that are capable of absorbing exudates at such a rate that they reach at least about 40%, preferably at least about 50%, and most preferably at least about 90% of their capacity in less than or equal to about 10 seconds. A suitable method for the percent rate of capacity is described in U.S. Pat. application Nos. 07/637,090 and 07/637,571 filed by Noel et al. and Feist, et al. In alternative embodiments, it is also possible for the high-speed absorbent gelling materials to be mixed with other types of absorbent gelling materials.

Preferably, in the embodiment described immediately above, the high-speed absorbent gelling materials are in fibrous form. Such fibers (though not necessarily high-speed absorbent gelling materials) are discussed more fully in U.S. Pat. No. 4,885,179. The term "fibrous absorbent gelling materials" as used herein, is intended to include absorbent gelling materials in the form of fibers that are comprised entirely of absorbent gelling material and bi-component fibers that comprised at least partially of other materials which have their surfaces coated with absorbent gelling materials. A suitable fibrous high speed absorbent gelling material is known as FIBERSORB SA7000 formerly manufactured by Arco Chemical Company of Newton Square, Pa.

The effective utilization of hydrogel-forming polymer gelling agents is believed to be improved in such a blended core. The use of higher concentrations of hydrogel-forming polymer gelling agents may also be possible.

The blended absorbent core 216 is preferably compressed to a density of at least about 0.06 gcm$^{-3}$ (1 g/ cubic inch) The blended core 216 may be compressed to densities at least as high as 0.25 gcm$^{-3}$ (4 g/cubic inch)to improve fluid wicking while still maintaining good softness and flexibility. (The density values specified above do not include the weight of any particles of absorbent gelling material.) Densification may be applied to the entire absorbent core 32 or only to selected portions. Patterned densification allows tailoring of the fluid handling properties to a specific need. For example, the density may be very low in the fluid target area to maximize fluid acquisition speed, and density my be very high near the core edges to maximize fluid wicking.

In one particularly preferred embodiment, the improved absorbent core 216 is an air-laid blend comprised of approximately 15% of 0.5 inch long, 15 denier per filament crimped polyester fibers and approximately 85% of cross-linked cellulose fibers compressed to a density of about 0.06 gcm$^{-3}$ (1 g/cubic inch).

The blended absorbent core 216 can be used as the entire core or it can be used as one or more layers in a layered construction. The blended absorbent core 216 can be used with or without an acquisition layer. The absorbent core can be used to produce a "profiled" absorbent article which is thicker in the center and tapers so it becomes thinner at the edges by stacking layers having relatively large length and width dimension on top of those with smaller length and widths.

In a layered construction, one or more layers can consist of all cellulose or cellulose/hydrogel-forming polymer material blends. The layers could also have differing fiber and/or absorbent gelling material content. For example, a higher percentage of absorbent gelling material could be provided in the lower layers to provide additional liquid storage capacity.

The blended absorbent core 216 is believed to provide enhanced performance. The blended absorbent core is believed to provide improved fluid acquisition speed and absorptive capacity. These improvements are believed to result in reduced leakage. The absorbent core can also be made smaller and thinner to make the article more comfortable and discrete to wear. The strength of the core is also believed to be improved because of the crimped or coiled synthetic fiber content. These improved characteristics are due to a number of factors.

Absorbent cores of the subject composition have a lower wet density than cores composed entirely of cellulose. The lower wet density results from the presence of the crimped or coiled synthetic fibers. Water is not absorbed into the synthetic fibers, therefore, the modulus of the fibers does not change when wetted and they do not collapse. The lower wet density provides the blended absorbent core with improved fluid acquisition speed and higher absorptive capacity. The lower wet density allows any hydrogel-forming polymer materials included in the fiber matrix to absorb a higher quantity of liquids since there is more room for the polymer materials to swell.

The first group of fibers is believed to aid in reducing leakage. The blended core provides a quantity of small capillaries which a core comprised of 100% large synthetic fibers would not have. These smaller capillaries allow the core to pull liquids through the topsheet and away from the wearer's skin. This improves leakage performance due to a reduction in the volume of fluid which can exit the product by running along the skin surface.

The first group of fibers of the blended core also provides a wicking capability. This capability results from the small capillaries mentioned above. This capillary can be enhanced by densification of the core. The cellulose allows the core to be maintained at a high density when dry that is generally not achievable with pure synthetics. The presence of the crimped or coiled synthetic fibers allows the portions of the core that are wetted to expand and this reduces the density of these portions. The neighboring densified areas which are still dry have a high density and provide small capillaries. The liquids will, as a result, tend to wick into these neighboring areas. This maintains absorptive capacity and acquisition speed.

The crimped or coiled synthetic fibers are believed to provide the core with improved compression resistance and resiliency. The resiliency maintains the void space in the core even after liquids are absorbed into the core and pressure is applied to the core. The void space provides additional storage space for absorbed liquids. It also provides additional space in which the absorbent gelling materials can swell after taking in liquids.

Further suitable core arrangements are described in U.S. Pat. Nos. 4,988,344, 4,988,345 and EP-A-0 198 683. Further possible core materials are described in U.S. Pat. No. 4,475,911. These documents are incorporated herein by reference. The sanitary napkin as shown in FIGS. 1 and 2, could also include any additional layers or other components such as are described in the above-mentioned publications. For example, the absorbent article may comprise an acquisition layer or patch of cross-linked cellulose fibers positioned between the topsheet 214 and the absorbent core 216.

Figure 3:
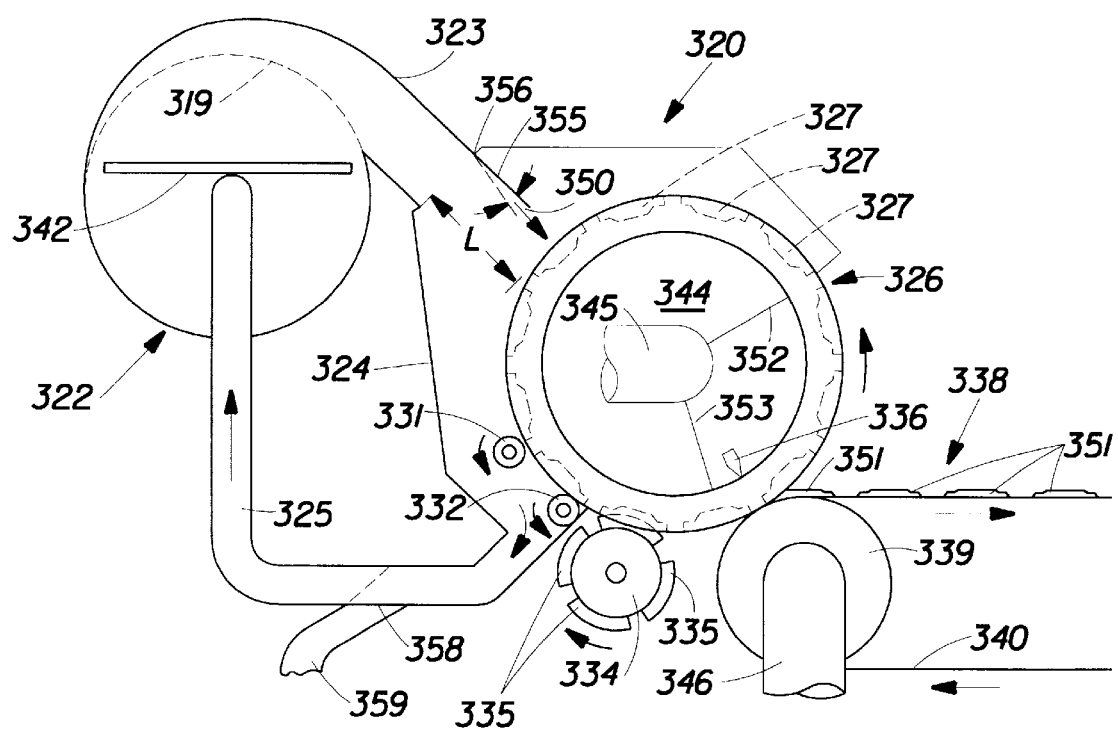

FIG. 3 shows a fragmentary portion of a drum-type apparatus for use in the method of making discrete absorbent cores of absorbent articles in accordance with the present invention. The apparatus 320 comprises a disc-type hammer mill 322 having a columnar discharge chute 323, a hood 324, a recirculation manifold 325, a deposition drum 326 having a plurality of deposition cavities 327 disposed in circumferentially spaced relationship, two scarfing rolls 331 and 332, a lugged cylinder 334 having a plurality of radially extending lugs 335, a blow-off means or nozzle 336 and a take-away conveyor 338 comprising a vacuum-type return roll 339 and a foraminous endless belt 340. Means not shown are provided for feeding the fiber board comprising the first and the second type of fibers into feed slot 342 of hammermill 322 at a pre-determined rate; means for powering and controlling hammermill 322; means for rotating drum 326, scarfing rolls 331 and 332, and conveyor 338 in timed relation, means for maintaining a pre-determined degree of vacuum in vacuum manifold 344 of drum 326 via vacuum duct 345, and means for maintaining a predetermined level of vacuum inside a sector of return roll 339 through vacuum duct: 346. Additionally, a somewhat columnar stream 350 of air-entrained fibers is shown in FIG. 3 to be exiting from the discharge chute 323 of hammermill 322 and directed generally radially towards a sector of drum 326 having a relatively small circumferential length; and an endless stream of discrete absorbent fibrous articles 351 is shown moving rightwardly on belt 340 or fake-away conveyor 338.

Briefly, apparatus 20 comprises means for converting and endless length or roll of fiber board, also referred to as a drylap web, into a stream of discrete fibrous articles having good edge definition and structural integrity. The hammermill disassociates the fibers of the fiber board and then discharges a relatively high velocity stream of air-entrained fibers through a filter means comprising a perforated plate 319, the stream being directed generally radially toward a relatively short circumferential span of the periphery of drum 326. The momentum of the fibers in the stream injects them into a deposition cavity disposed on the periphery of the drum while the substantially smaller momentum of the entrainment air enables the bulk of the entrainment air to turn upstream with respect to the periphery of the drum and be drawn through the foraminous bottom walls of substantially empty additional deposition cavities by the vacuum maintained in vacuum manifold 344 of drum 326. Each deposition cavity is preferably overfilled in its entirety and the excess is scarfed away by scarfing rolls 331 and 332. Then, the mass of fibers disposed in each filled deposition cavity is compacted a predetermined amount by the action of a lug 335 on the lugged cylinder 334 to complete the formation of a discrete airlaid article 351 having good edge definition and structural integrity as a result of being compacted before being removed from its deposition cavity. This also reduces the degree of length/width growth of the articles if they are subjected to calendering after being removed from their formation cavities. The discrete articles are then transferred to the take-away conveyor by joint action of this blow-off nozzle 336, and vacuum in a facing sector of the conveyor return roll 339. Parenthetically, the bulk of the entrainment air exits via substantially empty deposition cavities because of the flow impeding effect of the fiber build up in the deposition cavity passing under the stream 50 of air-entrained fibers.

The apparatus 320 further comprises an optional baffle plate 355 which is pivotally mounted on the upstream lip of chute 323 by pivot pin 356; a recirculation dump valve 358; and a recirculation dump duct 359. The angular positon of baffle plate 355 can be adjusted to precipitate a downstream velocity vector component to the stream 350 of fibers to match the peripheral velocity of drum 326, or to otherwise provide a sufficient downstream velocity vector component of stream 350 to achieve even filling of both ends of the deposition cavities 327. The recirculation dump valve 358, and the recirculation dump duct 359 are provided to divert air-entrained fibers from the recirculation manifold 325 when apparatus 320 is turned off to prevent fibers in the recirculation manifold from precipitating deleterious ramifications during start-up of apparatus 320.

In the apparatus 320, articles are formed in deposition cavities having lengths of about 17.8 cm and are spaced about 21.6 cm center-to-center about the periphery of the drum. The cavities are configured to be about 1.8 cm deep in their end regions and about 3.3 cm in their center spans in order to make articles 351. The hood wraps the drum approximately 180°, centered about the upstream wall of the discharge chute 323. The vacuum manifold 344 spans about 260° of the drum and is so disposed that its upstream end 352 is subjacent the upstream end of the hood and its downstream and 353 is positioned just upstream of the return roll 393 and nozzle 336. The lugged cylinder 334 is configured generally as shown in with four lugs 335. The lugs are disposed on the same pitch as the pitch of the deposition cavities on drum 326. A hammermill for use in the method according to the invention can be obtained from Curt G. Joa, Inc., for instance model number 85R-9505-B. The hammermill acts somewhat like a quasi centrifugal air blower in as much as it draws air into its intake. Thus, by connecting the recirculation manifold 25 to the intake of the hammermill, no other means need be provided to effect flow in the recirculation manifold.

Apparatus 320 is preferably operated with the stream 350 having a length L of up to about 35.6 cm and more preferably from about 25.4 to 30.5 cm; a velocity of stream 350 of from about 0.61 to 4.47 km.min$^{-1}$ and more preferably from 1.83 to 3.05 km.min$^{-1}$; a flow rate of stream 350 of from about 28.3 to about 42.5 m$^3$. min$^{-1}$; a fiber to air weight ratio in stream 350 of from about 6:1 to about 30:1, more preferably from about 7:1 to about 16:1; and a peripheral velocity of drum 326 preferably from about 76 to about 213 m.min$^{-1}$. The density of the fiber board, that is supplied to the hammer mill 320, either from a roll or as discrete boards, is between 0.4 and 0.6 gcm$^{-3}$, perferably between 0.45 and 0.50 gcm$^{-3}$ and has a caliper of between 1.2 and 1.9 mm, preferably obout 1.67 mm.

What is claimed is:

1. A method of making an absorbent batt, the method comprising the steps of:

providing a fiber board comprising a first type of fibers that are hydrophilic and a second type of fibers that are synthetic, multi-dimensional and crimped, said multi-dimensional, crimped synthetic fibers having an average extended length of between 2 and 25 mm, a denier of between 6 and 40, and between 3 and 8 crimps or coils per inch, said two types of fibers being mixed and compressed wherein said multi-dimensional, crimped synthetic fibers are able to be defiberized without being destroyed, the percentage of said multi-dimensional, crimped synthetic fibers in said fiber board being at least 10% by weight;

supplying said fiber board to a defiberising means for forming individualized fibers or groups of fibers;

defiberising said fiber board substantially without substantial plastic deformation of said multi-dimensional, crimped synthetic fibers; and transporting said defiberised fibers to a core forming means for forming an absorbent batt.

2. The method according to claim 1 wherein said synthetic fibers comprise polyethylene terephthalate.

3. The method according to claim 1 wherein said denier is between 10 and 20.

4. The method according to claim 1 wherein said synthetic fibers have a crimp angle between 80° and 120°.

5. The method according to claim 1 wherein said fibers are passed through a filter means after being defiberised.

6. The method according to claim 5 wherein said filter means comprises a perforated plate having apertures of a diameter that is equal to at least half said average extended length of said synthetic fibers.

7. The method according to claim 5 wherein said filter means comprise a plate having longitudinal slits having a length of at least said extended length of said synthetic fibers.

* * * * *